(12) United States Patent
Szarvas et al.

(10) Patent No.: US 8,163,951 B2
(45) Date of Patent: Apr. 24, 2012

(54) METHOD FOR PRODUCING QUATERNARY AMMONIUM COMPOUNDS

(75) Inventors: Laszlo Szarvas, Ludwigshafen (DE); Klemens Massonne, Bad Duerkheim (DE); Matthias Maase, Speyer (DE); Alfred Oftring, Bad Duerkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1084 days.

(21) Appl. No.: 11/597,106

(22) PCT Filed: May 27, 2005

(86) PCT No.: PCT/EP2005/005727
§ 371 (c)(1), (2), (4) Date: Nov. 20, 2006

(87) PCT Pub. No.: WO2005/115969
PCT Pub. Date: Dec. 8, 2005

(65) Prior Publication Data
US 2007/0254822 A1 Nov. 1, 2007

(30) Foreign Application Priority Data

May 28, 2004 (DE) .......................... 10 2004 026 153
Feb. 7, 2005 (DE) .......................... 10 2005 005 582

(51) Int. Cl.
*C07C 303/00* (2006.01)
*C07C 209/68* (2006.01)

(52) U.S. Cl. ............................... 558/39; 564/366
(58) Field of Classification Search .................. 510/178
See application file for complete search history.

(56) References Cited

U.S. PATENT DOCUMENTS

| 3,366,663 | A | * | 1/1968 | Plischke ..................... 558/39 |
| 3,371,117 | A | | 2/1968 | Campbell et al. |
| 4,572,769 | A | | 2/1986 | Shimizu et al. |
| 4,873,177 | A | | 10/1989 | Tanaka et al. |
| 5,153,348 | A | * | 10/1992 | Kerschner et al. ........... 558/276 |
| 2005/0070717 | A1 | | 3/2005 | Wasserscheid et al. |

FOREIGN PATENT DOCUMENTS

| DE | 37 05 896 A1 | | 8/1987 |
| DE | 10 2004 010 662.2 | | 3/2004 |
| EP | 1182196 | | 8/2000 |
| GB | 823 595 A | | 11/1959 |
| GB | 1297955 | | 11/1972 |
| JP | 57126465 | | 8/1982 |
| JP | 57126465 A | * | 8/1982 |
| WO | WO 02/12179 A1 | | 2/2002 |

OTHER PUBLICATIONS

Wilkes et al., "Air and Water Stable 1-Ehtyl-3-methylimidazolium Based Ionic Liquids", J Chem. Soc., Chem. Commun., 1992, pp. 965-667.

* cited by examiner

*Primary Examiner* — Necholus Ogden, Jr.
(74) *Attorney, Agent, or Firm* — Rothwell, Figg, Ernst & Manbeck, P.C.

(57) ABSTRACT

The present invention relates to a process for preparing quaternary ammonium compounds, which comprises reacting compounds comprising an $sp^3$-hybridized nitrogen atom with a dialkyl sulfate or trialkyl phosphate and subjecting the resulting ammonium compound to an anion exchange.

22 Claims, No Drawings

METHOD FOR PRODUCING QUATERNARY AMMONIUM COMPOUNDS

CROSS REFERENCE TO RELATED APPLICATION

This application is a 35 USC §371 National Phase Entry Application from PCT/EP 2005/005727, filed May 27, 2005, and designating the United States.

DESCRIPTION

The present invention relates to a process for preparing quaternary ammonium compounds, which comprises reacting compounds comprising an $sp^3$-hybridized nitrogen atom with a dialkyl sulfate or trialkyl phosphate and subjecting the resulting ammonium compound to an anion exchange.

Quaternary ammonium compounds are used in large quantities for various applications. Thus, quaternary ammonium compounds having at least one long alkyl chain display surface-active properties and are used as cationic surfactants, e.g. as wetting agents, antistatics, etc. Predominantly short-chain quaternary ammonium compounds have microbicidal properties and are therefore used in fungicidal and bactericidal disinfectants. In organic synthesis, quaternary ammonium compounds are used as phase transfer catalysts. In addition, there are various industrial uses of individual specific quaternary ammonium compounds. Salts made up of quaternary ammonium ions and suitable anions which are liquid at low temperatures (<100° C.) have now become more widely used as ionic liquids.

The increasing miniaturization of electronic components requires the provision of microchips having ever better performance and ever higher degrees of integration. These can be produced only from high-purity silicon wafers whose content of impurities is generally in a range up to at most 10 ppb and sometimes far below. The production of such electronic components involves process steps such as etching and cleaning in which the semiconductors are treated with various chemicals. For example, high-purity tetramethylammonium hydroxide is used for etching the reverse sides of silicon wafers and as developer for photoresists.

A substantial problem in the production of large-scale integrated circuits is contamination of the semiconductor surfaces by inorganic or organic compounds present in the chemicals used. For this reason, all reagents which come into contact with semiconductor elements have to meet extremely high purity requirements, e.g. the content of ionic impurities should be very low. The solutions preferably have a total metal content of not more than 5 ppb and sometimes less than 10 ppt for individual metal species. Contamination with certain anions also has to be avoided since these either have a corrosive action or complex metal ions and can thus alter the targeted doping of the semiconductor. The total content of such anions should generally not exceed 1 ppm.

For this reason, there is a great need for high-purity tetramethylammonium hydroxide solutions which are essentially free of undesirable organic compounds.

Processes for removing undesirable organic impurities from solutions of quaternary ammonium compounds, e.g. tetramethylammonium hydroxide solutions, are known but are generally complicated and correspondingly costly. There is thus a great need for processes which are suitable for the economical production of quaternary ammonium compounds which are substantially free of undesirable organic impurities.

It is known that amines can be alkylated by means of dialkyl sulfates, but in general only one alkyl group of the dialkyl sulfate is utilized, so that the corresponding monoalkylsulfate salts result. Thus, U.S. Pat. No. 3,366,663 describes a process for preparing tetraalkylammonium alkylsulfates in which a dialkyl sulfate, e.g. dimethyl sulfate, is reacted with a trialkylamine.

EP-A-1 182 196 describes a process for preparing ionic liquids, in which the amines, phosphines, imidazoles, pyridines, triazoles or pyrazoles on which the cation is based are alkylated by means of a dialkyl sulfate to give salts of the corresponding monoalkylsulfate anions and these are subsequently subjected to an anion exchange with metal salts.

WO 02/12179 describes a process for the sulfation of compounds having hydroxyl groups. Here, an ammonium monoorganylsulfate formed from a tertiary amine and a diorganylsulfate is used as sulfating agent.

In J. Chem. Soc., Chem. Commun., 1992, pp. 965-967, J. S. Wilkes and M. J. Zaworotko describe ionic liquids based on a 1-ethyl-3-methylimidazolium cation. Starting from the iodide compound, further anions, e.g. the sulfate in the form of its monohydrate, can be prepared by anion exchange with the corresponding silver salts.

WO 03/074494 describes halogen-free ionic liquids based on anions of the formula $[R'-O-SO_3]^-$ or $[R'-SO_3]^-$, where $R'$ is a group of the general formula $R^5-[X(-CH_2-)_n]_m$ in which n is from 1 to 12, m is from 1 to 400, X is oxygen, sulfur or a group of the general formula $-O-Si(CH_3)_2-O-$, $-O-Si(CH_2CH_3)_2-O-$, $-O-Si(OCH_3)_2-O-$ or $-O-Si(O-CH_2CH_3)_2-O-$ and $R^5$ is an optionally functionalized alkyl group. They are prepared from pyridine-$SO_3$ complexes and ethers of the formula $R'-OH$.

The Belgian patent BE 750 372 describes a process for preparing uncharged quaternary ammonium salts of polybasic acids, in which a quaternary ammonium salt of an acid ester of a polybasic acid, e.g. a tetraalkylammonium alkylsulfate, is hydrolyzed and subsequently treated with an alkali metal hydroxide.

JP-A-57 126465 describes a process for preparing tetraalkylammonium salts, in which a tetraalkylammonium alkylsulfate, e.g. tetraethylammonium ethylsulfate, is treated with an anion exchanger containing OH$^-$ anions and the resulting tetraalkylammonium hydroxide is neutralized with an acid.

DE-A-15 43 747 (U.S. Pat. No. 3,371,117) describes a process for the direct preparation of a bisquaternary ammonium salt from a dialkyl sulfate ester and a trialkylamine by reaction at a temperature in the range from 0 to 400° C. and a pressure which is sufficient to prevent vaporization of the amine. Since hydrolysis of the sulfate ester takes place at elevated temperatures, this document teaches carrying out the reaction in two stages, with one alkyl group of the sulfate ester initially participating in the alkylation at a low temperature in the range from about 0 to 50° C. and the second alkyl group then participating in a second step at elevated temperature in the range from about 50 to 400° C.

The unpublished German patent application 10 2004 010 662.2 describes a process for preparing ionic compounds comprising cations having quaternary $sp^2$-hybridized nitrogen atoms, in which compounds comprising a double-bonded nitrogen atom are reacted with a dialkyl sulfate at elevated temperature with participation of both alkyl groups of the dialkyl sulfate and, if appropriate, the resulting ionic compound containing sulfate anions is subjected to an anion exchange.

It is an object of the present invention to provide a simple and thus economical process for preparing quaternary ammonium compounds. In particular, the process should be suitable for preparing high-purity quaternary ammonium compounds, e.g. tetramethyl-ammonium hydroxide, which are substantially free of undesirable organic impurities. Especially, the quaternary ammonium compounds obtained in this way should be free of halogens, in particular free of chloride, bromide and iodide.

It has now surprisingly been found that this object is achieved by a process which comprises reacting an amine compound comprising at least one $sp^3$-hybridized nitrogen atom with a dialkyl sulfate to give a quaternary ammonium compound containing a sulfate anion as anion component and subsequently replacing the sulfate anion by a different anion.

The invention accordingly provides a process for preparing a quaternary ammonium compound, which comprises a) reacting an amine compound comprising at least one $sp^3$-hybridized nitrogen atom with a dialkyl sulfate or trialkyl phosphate to give a quaternary ammonium compound which has at least some polyvalent anions, and b) subjecting the quaternary ammonium compound obtained in step a) to an anion exchange.

It has surprisingly been found that amine compounds comprising at least one $sp^3$-hybridized nitrogen atom can be advantageously quaternized by means of dialkyl sulfates or trialkyl phosphates. Quaternary ammonium compounds having at least partly, preferably exclusively, polyvalent anions are obtained in this way. In a first preferred embodiment of this process, the amine compound is reacted in step a) with a dialkyl sulfate with participation of both alkyl groups of the dialkyl sulfate to give a quaternary ammonium compound having sulfate anions ($SO_4^{2-}$). In a second preferred embodiment of this process, the amine compound is reacted in step a) with a trialkyl phosphate with participation of two or three alkyl groups of the trialkyl phosphate to give a quaternary ammonium compound having phosphate anions ($PO_4^{3-}$) and/or monoalkylphosphate anions ($RPO_4^{2-}$ R=alkyl).

Quaternary ammonium compounds having doubly and/or triply negatively charged anions in place of singly negatively charged anions (monoalkylsulfate, dialkylphosphate) as anion component are thus obtained in an advantageous fashion. Thus, the alkyl group equivalents of the dialkyl sulfate or trialkyl phosphate can firstly be utilized effectively, and, secondly the resulting compounds having polyvalent anions are good intermediates for the preparation of quaternary ammonium compounds which are free of undesirable impurities, in particular halide-free quaternary ammonium compounds. The hydrolysis which is described in the prior art as a disadvantage in the double alkylation by means of dialkyl sulfates is advantageously not observed in the process of the invention. The use of complicated purification steps can thus generally be avoided.

For the purpose of explaining the present invention, the expression "alkyl" encompasses straight-chain and branched alkyl groups. It preferably refers to straight-chain or branched $C_1$-$C_{20}$-alkyl, preferably $C_1$-$C_{10}$-alkyl groups, particularly preferably $C_1$-$C_8$-alkyl groups and very particularly preferably $C_1$-$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The expression "alkyl" also encompasses substituted alkyl groups which generally have 1, 2, 3, 4 or 5 substituents, preferably 1, 2 or 3 substituents and particularly preferably 1 substituent. These are, for example, selected from among cycloalkyl, aryl, hetaryl, halogen, hydroxy, mercapto (sulfhydryl, thiol), amino, alkoxycarbonyl, acyl, nitro, aminocarbonyl, alkylaminocarbonyl, dialkylaminocarbonyl, alkylcarbonylamino, carboxylate, thioester and sulfonate.

The expression "alkylene" as used for the purposes of the present invention refers to straight-chain or branched alkanediyl groups which preferably have from 1 to 5 carbon atoms.

The expression "cycloalkyl" as used for the purposes of the present invention encompasses both unsubstituted and substituted cycloalkyl groups, preferably $C_5$-$C_8$-cycloalkyl groups, e.g. cyclopentyl, cyclohexyl or cycloheptyl. If they are substituted, these can generally bear 1, 2, 3, 4 or 5 substituents, preferably 1, 2 or 3 substituents. These substituents are, for example, selected from among alkyl and the substituents mentioned above for substituted alkyl groups.

The expression "heterocycloalkyl" as used for the purposes of the present invention encompasses saturated, cycloaliphatic groups which generally have from 4 to 7, preferably 5 or 6 ring atoms and in which 1, 2, 3 or 4 of the ring carbon atoms are replaced by heteroatoms selected from among the elements oxygen, nitrogen and sulfur and which may optionally be substituted. If they are substituted, these heterocycloaliphatic groups can bear, for example, 1, 2 or 3 substituents. These substituents are, for example, selected from among alkyl and the substituents mentioned above for substituted alkyl groups. Examples of such heterocycloaliphatic groups are pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl, dioxanyl.

The expression "aryl" as used for the purposes of the present invention encompasses both unsubstituted and substituted aryl groups, and preferably refers to phenyl, tolyl, xylyl, mesityl, naphthyl, fluorenyl, anthracenyl, phenanthrenyl or naphthacenyl, particularly preferably phenyl or naphthyl. If they are substituted, these aryl groups can generally bear 1, 2, 3, 4 or 5 substituents, preferably 1, 2 or 3 substituents. These substituents are, for example, selected from among alkyl and the substituents mentioned above for substituted alkyl groups.

The expression "hetaryl" as used for the purposes of the present invention encompasses unsubstituted or substituted, heterocycloaromatic groups, preferably the groups pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl and carbazolyl. If they are substituted, these heterocycloaromatic groups can generally have 1, 2 or 3 substituents. These substituents are, for example, selected from among alkyl and the substituents mentioned above for substituted alkyl groups.

For the purposes of the present invention, carboxylate and sulfonate are preferably derivatives of a carboxylic acid function or a sulfonic acid function, in particular a metal carboxylate or sulfonate, a carboxylic ester or sulfonic ester function or a carboxamide or sulfonamide function. They include, for example, esters with $C_1$-$C_4$-alkanols such as methanol, ethanol, n-propanol, isopropanol, n-butanol, sec-butanol and tert-butanol.

The above explanations of the expressions "alkyl", "cycloalkyl", "aryl", "heterocycloalkyl" and "hetaryl" apply analogously to the expressions "alkoxy", "cycloalkoxy", "aryloxy", "heterocycloalkoxy" and "hetaryloxy".

The expression "acyl" as used for the purposes of the present invention refers to alkanoyl or aroyl groups which generally have from 2 to 11, preferably from 2 to 8, carbon atoms, for example the acetyl, propanoyl, butanoyl, pentanoyl, hexanoyl, heptanoyl, 2-ethylhexanoyl, 2-propylheptanoyl, benzoyl or naphthoyl group.

The groups $NE^1E^2$ are preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Halogen is fluorine, chlorine, bromine and iodine, preferably fluorine, chlorine and bromine.

$M^+$ is a cation equivalent, i.e. a monovalent cation or the fraction of a polyvalent cation corresponding to a single positive charge. The cation $M^+$ serves merely as counterion to balance the charge of negatively charged substituent groups such as $COO^-$ or the sulfonate group and can in principle be chosen at will. Preference is therefore given to using alkali metal ions, in particular $Na^+$, $K^+$, $Li^+$ ions, or onium ions such as ammonium, monoalkylammonium, dialkylammonium, trialkylammonium, tetraalkylammonium, phosphonium, tetraalkylphosphonium or tetraarylphosphonium ions.

An analogous situation applies to the anion equivalent $A^-$ which serves merely as counterion for positively charged substituent groups such as the ammonium groups and can be chosen at will among monovalent anions and the fractions of a polyvalent anion corresponding to a single negative charge, with preference generally being given to anions other than halide ions.

For the purposes of the present invention, the term polycyclic compounds encompasses in the widest sense compounds which comprise at least two rings, regardless of how these rings are linked. The rings can be carbocyclic and/or heterocyclic. The rings can be linked via single or double bonds ("multinuclear compounds"), joined by fusion ("fused ring systems") or bridged ("bridged ring systems", "cage compounds"). Fused ring systems can be (fused-on) aromatic, hydroaromatic and cyclic compounds linked by fusion. Fused ring systems have two, three or more than three rings. Depending on the way in which the rings are linked, a distinction is made in the case of fused ring systems between ortho-fusion, i.e. each ring shares an edge or two atoms with each adjacent ring, and peri-fusion in which a carbon atom belongs to more than two rings. The bridged ring systems include, for the purposes of the present invention, those which do not belong to the multinuclear ring systems and fused ring systems and in which at least two ring atoms belong to at least two different rings. In the case of the bridged ring systems, a distinction is made, depending on the number of ring opening reactions formally required to obtain an open-chain compound, between bicyclo, tricyclo, tetracyclo compounds, etc., which comprise two, three, four, etc. rings. The bridged ring systems can, if desired, additionally have, depending on size, one, two, three or more than three fused-on rings.

The process of the invention is quite generally suitable for preparing ionic compounds of the formula I

   (I)

where
$B^{m+}$ is an m-valent cation having at least one quaternary $sp^3$-hybridized nitrogen atom,
$X^{n-}$ is an n-valent anion,
b and x are integers $\geq 1$, with the proviso that (b times m)=(x times n).

Compounds of this type include compounds of the formulae $B^+X^-$, $B^{m+}X^{m-}$, $nB^+X^{n-}$ and $B^{m+}mX^-$, where m and n are integers >1.

The anion component $X^{n-}$ is preferably an anion other than $Cl^-$, $Br^-$, $I^-$ and monoalkylsulfates and monoalkylphosphates. The anions $X^{n-}$ are preferably selected from among hydroxide ($OH^-$), sulfate ($SO_4^{2-}$), hydrogensulfate ($HSO_4^-$), nitrite ($NO_2^-$), nitrate ($NO_3^-$), cyanide ($CN^-$), cyanate ($OCN^-$), isocyanate ($NCO^-$), thiocyanate ($SCN^-$), isothiocyanate ($NCS^-$), phosphate ($PO_4^{3-}$), hydrogenphosphate ($HPO_4^{2-}$), dihydrogenphosphate ($H_2PO_4^-$), primary phosphite ($H_2PO_3^-$), secondary phosphite ($HPO_3^{2-}$), orthoborate ($BO_3^{3-}$), metaborate (($BO_2)_3^{3-}$) pentaborate $B_5O_8^-$, pentaborate hydrate ($B_5H_4O_{10}^-$), $B_5O_6^-$, tetrafluoroborate ($[BF_4]^-$), tetrachloroborate ($[BCL_4]^-$), tetraphenylborate ($[B(C_6H_5)_4]^-$), hexafluorophosphate ($[PF_6]^-$), hexafluoroantimonate ($[SbF_6]^-$), hexafluoroarsenate ($[AsF_6]^-$), tetrachloroaluminate ($[AlCl_4]^-$), tetrabromoaluminate ($[AlBr_4]^-$), trichlorozincate ($[ZnCl_3]^-$), dichlorocuprates(I) and (II), carbonate ($CO_3^{2-}$), hydrogencarbonate ($HCO_3^-$), fluoride ($F^-$), triorganylsilanolate $R'_3SiO^-$, fluorosulfonate ($CF_3-SO_3^-$), sulfonate ($R'-SO_3$)$^-$ and $[(R'-SO_2)_2N]^-$, where R' is alkyl, cycloalkyl or aryl. R is preferably a linear or branched aliphatic or alicyclic alkyl radical comprising from 1 to 12 carbon atoms or a $C_5$-$C_{18}$-aryl, $C_5$-$C_{18}$-aryl-$C_1$-$C_6$-alkyl or $C_1$-$C_6$-alkyl-$C_5$-$C_{18}$-aryl radical which may be substituted by halogen atoms.

$X^{n-}$ is particularly preferably $OH^-$.

The amine compound comprising at least one $sp^3$-hybridized nitrogen atom which is used in step a) can be an acyclic or cyclic compound. The cation component $B^{m+}$ is derived from these amines by quaternization.

Suitable amine compounds have at least one primary, secondary or tertiary amino function. They are preferably selected from among compounds of the general formula $NR^1R^2R^3$, where $R^1$, $R^2$ and $R^3$ are selected independently of one another from among hydrogen, alkyl, cycloalkyl, heterocycloalkyl, aryl and hetaryl, with at least two of the radicals $R^1$, $R^2$ and $R^3$ together with the N atom to which they are bound also being able to be part of a polycyclic compound.

The radicals $R^1$, $R^2$ and $R^3$ are preferably selected independently of one another from among hydrogen, $C_1$-$C_{30}$-alkyl, $C_3$-$C_8$-cycloalkyl, $C_3$-$C_8$-heterocycloalkyl, $C_1$-$C_{14}$-aryl and $C_1$-$C_{14}$-heteroaryl radicals.

When at least one of the radicals $R^1$ to $R^3$ is alkyl, it is preferably a $C_1$-$C_{20}$-alkyl radical which, as defined above, may be substituted and/or interrupted by 1, 2, 3 or more than 3 nonadjacent heteroatoms or heteroatom-containing groups. The heteroatoms and heteroatom-containing groups are preferably selected from among O, S, $NR^4$ and $PR^5$, where $R^4$ and $R^5$ are each, independently of one another, hydrogen, alkyl, cycloalkyl, heterocycloalkyl, aryl, hetaryl, $COOR^a$, $COO^-M^+$, $SO_3R^a$, $SO_3^-M^+$, sulfonamide, $NE^1E^2$, $(NE^1E^2E^3)^+A^-$, $OR^a$, $SR^a$, $(CHR^bCH_2O)_yR^a$, $(CH_2O)_yR^a$, $(CH_2CH_2NE^1)_yR^a$, alkylaminocarbonyl, dialkylaminocarbonyl, alkylcarbonylamino, halogen, nitro, acyl or cyano, where
the radicals $R^a$ are identical or different radicals selected from among hydrogen, alkyl, cycloalkyl, aryl, heterocycloalkyl and hetaryl,
$E^1$, $E^2$, $E^3$ are identical or different radicals selected from among hydrogen, alkyl, cycloalkyl, aryl and hetaryl, $R^b$ is hydrogen, methyl or ethyl, $M^+$ is a cation equivalent, $A^-$ is an anion equivalent and y is an integer from 1 to 250.

When at least one of the radicals $R^1$ to $R^3$ is substituted alkyl, the substituents are preferably selected from among hydroxy, mercapto, ester and thioester.

Suitable radicals $R^1$ to $R^3$ are, for example, hydrogen, methyl, ethyl, n-propyl, sec-propyl, isopropyl, n-butyl, isobutyl, sec-butyl, tert-butyl, n-pentyl and n-hexyl, lauryl, tridecyl, myristyl, palmityl and stearyl. Further suitable radicals $R^1$ to $R^3$ are 5-, 6-and 7-membered saturated, unsaturated or aromatic carbocycles and heterocycles, e.g. cyclopentyl, cyclohexyl, phenyl, tolyl, xylyl, cycloheptanyl, naphthyl, tetrahydrofuranyl, tetrahydropyranyl, dioxanyl, pyrrolidyl, piperidyl, pyridyl and pyrimidyl.

Suitable amine compounds having a primary amino function are, for example, methylamine, ethylamine, n-propylamine, isopropylamine, n-butylamine, isobutylamine, sec-butylamine, tert-butylamine, pentylamine, hexylamine, cyclopentylamine, cyclohexylamine, aniline and benzylamine.

Suitable amine compounds which have a primary amino function and in which one of the radicals $R^1$ to $R^3$ is an alkyl radical interrupted by O are, for example, $CH_3$—O—$C_2H_4$—$NH_2$, $C_2H_5$—O—$C_2H_4$—$NH_2$, $CH_3$—O—$C_3H_6$—$NH_2$, $C_2H_5$—O—$C_3H_6$—$NH_2$, n-$C_4H_9$—O—$C_4H_8$—$NH_2$, HO—$C_2H_4$—$NH_2$, HO—$C_3H_7$—$NH_2$ and HO—$C_4H_8$—$NH_2$.

Suitable amine compounds having a secondary amino function are, for example, dimethylamine, diethylamine, methylethylamine, di-n-propylamine, diisopropylamine, diisobutylamine, di-sec-butylamine, di-tert-butylamine, dipentylamine, dihexylamine, dicyclopentylamine, dicyclohexylamine and diphenylamine. Suitable amine compounds which have a secondary amino function and in which one or two of the radicals $R^1$ to $R^3$ is/are an alkyl radical interrupted by O are, for example, $(CH_3$—O—$C_2H_4)_2NH$, $(C_2H_5$—O—$C_2H_4)_2NH$, $(CH_3$—O—$C_3H_6)_2NH$, $(C_2H_5$—O—$C_3H_6)_2NH$, (n-$C_4H_9$—O—$C_4H_8)_2NH$, (HO—$C_2H_4)_2NH$, (HO—$C_3H_6)_2NH$ and (HO—$C_4H_8)_2NH$.

Suitable amine compounds having a tertiary amino function are, for example, trimethylamine, triethylamine, tri(n-propyl)amine, tri(isopropyl)amine, tri(n-butyl)amine, tri(isobutyl)amine, tri(tert-butyl)amine, etc.

Further suitable amine compounds having a tertiary amino function are dialkyl-arylamines, preferably di($C_1$-$C_4$-)alkylarylamines, in which the alkyl groups and/or the aryl group may be additionally substituted. The aryl group is preferably phenyl. Such amine compounds include, for example, N,N-dimethylaniline, N,N-diethylaniline, N,N,2,4,6-pentamethylaniline, bis(4-(N,N-dimethylamino)phenyl)methylene, 4,4'-bis(N,N-dimethylamino)benzophenone, etc.

Further suitable amine compounds having a tertiary amino function are alkyldiarylamines, preferably ($C_1$-$C_4$-)alkyldiarylamines, in which the alkyl group and/or the aryl groups may be substituted. Such amine compounds include, for example, diphenylmethylamine and diphenylethylamine.

Further suitable amine compounds having a tertiary amino function are triarylamines, in which the aryl groups may be substituted, e.g. triphenylamine, etc. Other preferred amines are tricycloalkylamines such as tricyclohexylamine.

When at least two of the radicals $R^1$, $R^2$ and $R^3$ together with the N atom to which they are bound are part of a polycyclic compound, preference is given to two of the radicals $R^1$, $R^2$ and $R^3$ together with the N atom to which they are bound forming an optionally substituted 5-to 7-membered heterocycle which can contain one, two or three further heteroatoms or heteroatom-containing groups selected from among O, S, $NR^4$ and $PR^5$, where $R^4$ and $R^5$ are as defined above. Suitable cyclic amine compounds are, for example, pyrrolidine, piperidine, morpholine and piperazine and also their substituted derivatives. Suitable derivatives of the abovementioned nitrogen-containing heterocycles can, for example, have one or more $C_1$-$C_6$-alkyl substituents such as methyl, ethyl, n-propyl, isopropyl, n-butyl, sec-butyl, tert-butyl, etc. They include, for example, the N—$C_1$-$C_6$-alkyl derivatives.

Preference is also given to the radicals $R^1$, $R^2$ and $R^3$ together with the N atom to which they are bound forming a bicyclic trialkylenamine or trialkylenediamine, e.g. 1-azabicyclo[2.2.2]octane or 1,4-diazabicyclo[2.2.2]octane.

Further suitable amine compounds are alkylenediamines, dialkylenetriamines, trialkylenetetramines and polyalkylenepolyamines such as oligoalkylenimines or polyalkylenimines, in particular oligoethylenimines or polyethylenimines, preferably oligoethylenimines having from 2 to 20, preferably from 2 to 10 and particularly preferably from 2 to 6, ethylenimine units. Suitable compounds of this type are, in particular, n-propylenediamine, 1,4-butanediamine, 1,6-hexanediamine, diethylenetriamine, triethylenetetramine and polyethyleneimines, and also their alkylation products which have at least one primary or secondary amino function, e.g. 3-(dimethylamino)-n-propylamine, N,N-dimethylethylenediamine, N,N-diethylethylenediamine and N,N,N',N'-tetramethyldiethylenetriamine. Ethylenediamine is likewise suitable.

Further suitable amine compounds are the reaction products of alkylene oxides, in particular ethylene oxide and/or propylene oxide, with primary and secondary amines.

The process of the invention can be advantageously used for preparing quaternary ammonium compounds from amino alcohols, amino mercaptans and esters thereof. The esters are preferably esters of inorganic acids, especially sulfuric acid and phosphoric acid, or derivatives of these esters. The amine compound used in step a) then has at least one substituent selected from among hydroxyl groups, mercapto groups, ester groups, thioester groups and combinations thereof in addition to the amino function. The process of the invention thus makes it possible for the first time to prepare quaternary ammonium compounds from amino alcohols, amino mercaptans and esters thereof which are free of $Cl^-$, $Br^-$, $I^-$ and at the same time free of monoalkylsulfate anions and monoalkylphosphate anions.

Suitable amino alcohols are, for example, 2-aminoethanol (=monoethanolamine), 3-amino-1-propanol, 2-amino-1-propanol, 1-amino-2-propanol, 2-amino-3-phenylpropanol, 2-amino-2-methyl-1-propanol, 2-amino-1-butanol, 4-amino-1-butanol, 2-aminoisobutanol, 2-amino-3-methyl-1-butanol, 2-amino-3,3-dimethylbutanol, 1-amino-1-pentanol, 5-amino-1-pentanol, 2-amino-1-pentanol, 2-amino-4-methyl-1-pentanol, 2-amino-3-methyl-1-pentanol, 2-aminocyclohexanol, 4-aminocyclohexanol, 3-(aminomethyl)-3,5,5-trimethylcyclohexanol, 2-amino-1,2-diphenylethanol, 2-amino-1,1-diphenylethanol, 2-amino-2-phenylethanol, 2-amino-1-phenylethanol, 2-(4-aminophenyl)ethanol, 2-(2-aminophenyl)ethanol, 1-(3-aminophenyl)ethanol, 2-amino-1-hexanol, 6-amino-1-hexanol, 6-amino-2-methyl-2-heptanol, N-methylisopropanolamine, N-ethylisopropanolamine, N-methylethanolamine, N-ethylethanolamine, N-(3-hydroxypropyl)methylamine, N-(2-hydroxyethyl)dimethylamine, N-(3-hydroxypropyl)dimethylamine, N-(2-hydroxyethyl)diethylamine, N-(3-hydroxypropyl)diethylamine, 1-ethylaminobutan-2-ol, 4-methyl-4-aminopentan-2-ol, 2-(2-aminoethoxy)ethanol, N-(2-hydroxyethyl)piperazine, 1-amino-2-indanol, N-(2-hydroxyethyl)aniline, amino sugars such as D-glucosamine, D-galactosamine, 4-amino-4,6-didesoxy-α-D-glucopyranose, N-(2-hydroxyethyl)ethylenediamine, diethanolamine, dipropanolamine, diisopropanolamine, 2-amino-1,3-propanediol, 3-amino-1,2-propanediol, and mixtures thereof.

A particular embodiment of the process of the invention is employed for preparing quaternary ammonium compounds from N-(hydroxyalkyl)dialkylamines and specifically from N-(2-hydroxyethyl)dimethylamine (dimethylaminoethanol). Quaternary ammonium compounds of N-(2-hydroxyethyl) dimethylamine, i.e. choline (=(2-hydroxyethyl)trimethylammonium hydroxide) and other salts (cholinium salts) have become widespread in pharmacy, the animal feed industry, as dietary (nutritional) supplement, etc., and there is a correspondingly high demand for halogen-free cholinium salts.

Suitable amine compounds a) having at least one mercapto group are, for example, 2-mercaptoethylamine, 3-mercaptopropylamine, 4-mercaptobutylamine, N-(2-mercaptoethyl) methylamine, N-(2-mercaptoethyl)dimethylamine, etc.

Further suitable amine compounds a) are the esters of amino alcohols and amino thiols with inorganic acids and also derivatives thereof. These are, in particular, esters of dimethylaminoethanol with sulfuric acid, phosphoric acid and derivatives thereof. The process of the invention is thus specifically suitable for the preparation of choline O-phosphate (phosphorylcholine), choline O-sulfate (sulfurylcholine) and O-phosphatidylcholine (lecithin). The abovementioned compounds all have a betaine structure. Phosphorylcholine improves the biocompatibility of materials and is therefore used for coating contact lenses and in modern medicine, e.g. for implants, bypasses (coronary stents), cannulae, etc. Furthermore, the compounds mentioned and their derivatives are used in the food industry, e.g. for producing baby food and dietary (nutritional) supplements, and also in cosmetics. There is therefore a great need for processes for preparing them in very pure, specifically halogen-free, form.

The abovementioned amine compounds are preferably used individually. However, they can also be used in the form of any mixtures.

To prepare ionic compounds comprising at least one cation having a quaternary $sp^3$-hybridized nitrogen atom according to the invention, a compound comprising an $sp^3$-hybridized nitrogen atom is reacted with a dialkyl sulfate or trialkyl phosphate in a first reaction step a) to give a quaternary ammonium compound having at least some polyvalent anions and the ionic compound obtained in step a) is subsequently subjected to an anion exchange in step b).

According to the invention, the reaction in step a) is carried out at an elevated temperature, i.e. at a temperature above ambient temperature. The temperature in step a) is preferably at least 40° C., particularly preferably at least 80° C. The reaction in step a) is preferably carried out at a temperature in the range from >100 to 220° C., particularly preferably from 120 to 200° C.

In a preferred embodiment, step a) is carried out by firstly bringing the amine compound into contact with the dialkyl sulfate or the trialkyl phosphate at a temperature of not more than 30° C. and subsequently heating the resulting mixture to a temperature of at least 40° C. to bring about the further reaction, as described above. The amine compound is preferably brought into contact with the dialkyl sulfate or trialkyl phosphate at a temperature of not more than 20° C., in particular at a temperature of not more than 10° C. The amine compound is preferably brought into contact with the dialkyl sulfate or trialkyl phosphate in portions. For this purpose, the amine or the dialkyl sulfate/trialkyl phosphate can be placed in a reaction vessel and the other component can be added in portions. Preference is given to both components being used in liquid form, i.e. in the form of an aqueous solution. For the purposes of the present invention, an aqueous solution includes water and mixtures of water with water-miscible solvents.

The reaction in step a) is generally carried out under superatmospheric pressure. The reaction is preferably carried out under the intrinsic pressure of the reaction mixture under the reaction conditions. When volatile amines are used, the pressure during the reaction in step a) is generally at least 1.5 bar, in particular at least 2 bar. If desired, the pressure during the reaction in step a) can be up to 300 bar. Suitable pressure-rated reactors are known to those skilled in the art and are described, for example, in Ullmanns Enzyklopädie der technischen Chemie, Volume 1, 3rd edition, 1951, p. 769 ff. In general, an autoclave which may be provided with a stirring facility and/or an internal lining is used for the process of the invention.

When at least one dialkyl sulfate is used as alkylating agent, the molar ratio of the amine compound to be alkylated to the dialkyl sulfate is preferably at least 2:1. The molar ratio of the amine compound to the dialkyl sulfate is particularly preferably in the range from 1.8:1 to 10:1, in particular from 2.05:1 to 5:1, especially from 2.1:1 to 3:1.

When at least one trialkyl phosphate is used as alkylating agent, the molar ratio of the amine compound to be alkylated to the trialkyl phosphate is preferably at least 2:1. The molar ratio of the amine compound to the trialkyl phosphate is particularly preferably in the range from 3:1 to 5:1.

The reaction of the compound to be alkylated with the dialkyl sulfate or trialkyl phosphate can be carried out in bulk or preferably in the presence of a solvent which is inert under the reaction conditions. Suitable solvents are, for example, water, water-miscible solvents, for example alcohols such as methanol and ethanol, and mixtures thereof. Preference is given to using water or a solvent mixture comprising at least 30% by volume, preferably at least 50% by volume, in particular at least 80% by volume, of water as solvent.

The dialkyl sulfates used in step a) are preferably di-$C_1$-$C_{10}$-alkyl sulfates and in particular di-$C_1$-$C_6$-alkyl sulfates such as dimethyl sulfate, diethyl sulfate, di-n-propyl sulfate, diisopropyl sulfate, di-n-butyl sulfate, diisobutyl sulfate, di-tert-butyl sulfate, di-n-pentyl sulfate, diisopentyl sulfate, dineopentyl sulfate and di-n-hexyl sulfate. Particular preference is given to using dimethyl sulfate and diethyl sulfate.

The trialkyl phosphates used in step a) are preferably tri-$C_1$-$C_{10}$-alkyl phosphates and in particular tri-$C_1$-$C_6$-alkyl phosphates such as trimethyl phosphate, triethyl phosphate, tri-n-propyl phosphate, triisopropyl phosphate, tri-n-butyl phosphate, triisobutyl phosphate, tri-tert-butyl phosphate, tri-n-pentyl phosphate, triisopentyl phosphate, trineopentyl phosphate and tri-n-hexyl phosphate. Particular preference is given to using trimethyl phosphate and triethyl phosphate.

If desired, the reaction in step a) can be carried out in the presence of at least one inert gas. Suitable inert gases are, for example, nitrogen, helium and argon.

The reaction in step a) can be carried out continuously or batchwise.

The quaternary ammonium salts can be isolated from the reaction mixture obtained in step a) by customary methods known to those skilled in the art. This is done especially when the reaction in step b) is to be carried out in a different solvent than is the alkylation in step a). If a solvent has been used for the reaction in step a), this can be removed by evaporation, preferably under reduced pressure. Since the ionic compounds obtained are nonvolatile, the pressure range employed is generally not critical. If a virtually complete removal of the solvent is desired, it is possible to employ, for example, a fine vacuum of from $10^1$ to $10^{-1}$ Pa or a high vacuum of from $10^{-1}$ to $10^{-5}$ Pa. To generate the pressure, it is possible to use customary vacuum pumps such as liquid jet vacuum pumps, rotary vane and rotary piston vacuum pumps, diaphragm vacuum pumps, diffusion pumps, etc. The removal of the solvent can also be carried out at an elevated temperature of up to 150° C., preferably up to 100° C.

The reaction mixture obtained in step a) is preferably used for the reaction in step b) without prior isolation.

The anion exchange in step b) can be effected by transprotonation, reaction with a metal salt, ion exchange chromatography, electrolytically or by means of a combination of these measures.

In a first embodiment, the quaternary ammonium compound obtained in step a) of the process of the invention, which has at least some polyvalent anions, is reacted with an acid, preferably sulfuric acid or phosphoric acid, with proton transfer.

To carry out the transprotonation, a quaternary ammonium compound having sulfate anions is preferably reacted with sulfuric acid to give the corresponding hydrogen sulfates ($X^{n-}=HSO_4^-$). The transprotonation is preferably carried out using 100% strength $H_2SO_4$. The molar ratio of $H_2SO_4$ to $SO_4^{2-}$ is preferably $\geq 1:1$ and is, for example, in a range from 1:1 to 2:1.

Furthermore, preference is also given to carrying out the transprotonation by reacting a quaternary ammonium compound having phosphate or monoalkylphosphate anions with phosphoric acid to give the corresponding hydrogenphosphates ($X^{n-}=HSO_4^{2-}$) and/or dihydrogenphosphates ($X^{n-}=H_2PO_4^-$). The molar ratio of $H_3PO_4$ to anions to be replaced is preferably $\geq 1:1$ and is, for example, in a range from 1:1 to 2:1.

In a further embodiment, the anion exchange in step b) is effected by reaction with a metal salt. This reaction is preferably carried out in a solvent from which a metal sulfate formed from the metal of the metal salt and the sulfate anion crystallizes. The above-described hydrogensulfates can also be used for this variant of the anion exchange. The cation of the metal salt is preferably an alkali metal, alkaline earth metal, lead or silver ion. The anion of the metal salt is selected from among the abovementioned anions $X^{n-}$, in particular anions other than $Cl^-$, $Br^-$, $I^-$, monoalkylsulfate and monoalkylphosphate. In a suitable procedure, a solution of the metal salt is brought into contact with a solution of the quaternary ammonium compound. Suitable solvents are, for example, water, water-miscible solvents, for example alcohols such as methanol and ethanol, and mixtures thereof. The reaction temperature is preferably in a range from –10 to 100° C., in particular from 0 to 80° C.

In a further embodiment, the anion exchange in step b) is effected by ion exchange chromatography. The basic ion exchangers which are known to those skilled in the art and comprise at least one base immobilized on a solid phase are in principle suitable for this purpose. The solid phase of these basic ion exchangers comprises, for example, a polymer matrix. Such matrices include, for example, polystyrene matrices comprising styrene together with at least one crosslinking monomer, e.g. divinylbenzene, and also, if appropriate, further comonomers in copolymerized form.

Also suitable are polyacrylic matrices which are obtained by polymerization of at least one (meth)acrylate, at least one crosslinking monomer and, if appropriate, further comonomers. Suitable polymer matrices are also phenol-formaldehyde resins and polyalkylamine resins obtained, for example, by condensation of polyamines with epichlorohydrin.

The anchor groups (whose loosely bound counterions can be replaced by ions bearing a charge of the same sign) bound directly or via a spacer group to the solid phase are preferably selected from among nitrogen-containing groups, preferably tertiary and quaternary amino groups.

Suitable functional groups are, for example (in order of decreasing basicity):
— $CH_2N^+(CH_3)_3$ $OH^-$ e.g. Duolite A 101
— $CH_2N^+(CH_3)_2CH_2CH_2OH$ $OH^{31}$ e.g. Duolite A 102
— $CH_2N(CH_3)_2$ e.g. Amberlite IRA 67
— $CH_2NHCH_3$
— $CH_2NH_2$ e.g. Duolite A 365

Both strongly basic and weakly basic ion exchangers are suitable for the process of the invention but preference is given to strongly basic ion exchangers in OH form. Among the weakly basic ion exchangers, preference is given to those bearing tertiary amino groups. Strongly basic ion exchangers generally have quaternary ammonium groups as anchor groups. Commercially available ion exchangers suitable for the process of the invention include, for example, Amberlyst® A21 (dimethylamino-functionalized, weakly basic) and Amberlyst® A27 (quaternary ammonium groups, strongly basic) and Ambersep® 900 OH (strongly basic). For the ion exchange, the ion exchangers are firstly loaded with the desired anions $X^{n-}$ and subsequently brought into contact with the ionic compounds based on sulfate anions or phosphate anions (or hydrogensulfate anions, hydrogenphosphate anions and/or dihydrogenphosphate anions).

In a further embodiment, the anion exchange in step b) is effected by electrolysis (electrodialysis). The use of electrolysis cells having ion-exchange membranes thus allows, for example, the preparation of bases from the corresponding salts. Suitable electrodialysis cells and membranes for the anion exchange and also bipolar membranes for the simultaneous exchange of cations and anions are known and commercially available (e.g. from FuMA-Tech St. Ingbert, Germany; Asahi Glass; PCA-Polymerchemie Altmeier GmbH und PCCell GmbH, Lebacher Straße 60, D-66265, Heusweiler, Germany). In this embodiment, too, the fact that quaternary ammonium compounds having polyvalent, noncorrosive anions are formed in step a) of the process of the invention is found to have a particularly advantageous effect on the life of the electrolysis apparatuses used, especially the membranes.

A first group of suitable electrolysis cells for the anion exchange are cells in which the electrode compartments are separated from one another by a membrane. Suitable membranes are, for example, membranes based on perfluoropolymers. Further suitable electrolysis cells for the anion exchange are ones in which the electrode compartments are not separated from one another by a membrane. These include, for example, "capillary gap cells" (CGC) which comprise, for example, a bipolar stack of electrode discs comprising, for example, graphite or graphite-modified polymers. "Solid polymer electrolyte (SPE) cells" which require no additional electrolyte are also suitable.

In an embodiment of the process for preparing quaternary ammonium hydroxides, a quaternary ammonium compound containing sulfate anions, monoalkylphosphate anions or phosphate anions obtained by step a) of the process of the invention can, for example, be converted electrolytically into the corresponding quaternary ammonium hydroxide. If desired, the electrolytic anion exchange can be followed by ion exchange chromatography. This makes it possible to obtain highly pure quaternary ammonium compounds which contain only extremely low concentrations or concentrations below the detection limit of undesirable anions.

The process of the invention makes it possible for the first time to prepare compounds of the general formula b $B^{m+}x X^n$ (I), as defined above, which are free of $Cl^-$, $Br^{31}$, $I^{31}$ and at the same time free of monoalkylsulfate anions and monoalkylphosphate anions. To prepare compounds of the formula I having an extremely low residual content of halide ions, the reaction in steps a) and b) is preferably carried out with the exclusion of halide ions and of materials which liberate these. Thus, reagents, solvents, inert gases, etc., which are substantially free of halide ions can be used for the reaction. Such components are commercially available or can be prepared by customary purification methods known to those skilled in the art. These include, for example, adsorption, filtration and ion exchange processes. If desired, the apparatuses used in steps a) and b) can also be freed of halide ions before use, e.g. by rinsing with halide-free solvents. The process of the invention makes it possible to obtain compounds of the general formula I in which $X^{n-}$ is $OH^-$ and the total content of halide ions is not more than 100 ppm, preferably not more than 10 ppm and in particular not more than 1 ppm. Furthermore, it is possible to obtain compounds which have a total content of monoalkylsulfate anions of not more than 100 ppm, preferably not more than 10 ppm and in particular not more than 1 ppm.

The invention further provides a process for preparing high-purity aqueous tetraalkyl-ammonium hydroxide solutions, wherein, in each case in water and in the absence of compounds and of materials which comprise or liberate halide ions, a) a trialkylamine compound is reacted with a dialkyl sulfate with participation of both alkyl groups of the dialkyl sulfate to give a high-purity aqueous tetraalkyl-ammonium salt solution and b) the tetraalkylammonium salt solution obtained in step a) is subjected to an electrolytic anion exchange or ion exchange chromatography to replace the sulfate anions by hydroxide ions.

In the abovementioned process, preference is given to reacting trimethylamine with dimethyl sulfate to give a high-purity aqueous tetramethylammonium hydroxide solution.

The invention further provides for the use of a high-purity tetramethylammonium hydroxide solution having a total halide ion content of not more than 100 ppb in the electronics industry, for the treatment of substrates of electronic components, in particular for the treatment of semiconductor components. Thus, tetramethylammonium hydroxide solutions can advantageously be used for etching silicon wafers. They are capable of anisotropic etching in which the etching rate is dependent on the crystal direction of the silicon. The individual crystal planes can act as lateral etching stoppers in the removal of the silicon, as a result of which high structural accuracy is achieved.

The invention further provides a high-purity aqueous tetramethylammonium hydroxide solution for the treatment of substrates of electronic components which contains not more than 100 ppb toc of halide ions.

The invention is illustrated by the following nonlimiting examples.

EXAMPLES

Example 1 a) Preparation of N,N-dimethylpiperidinium sulfate by reaction in water 172.9 ml of distilled water and 31.7 g (0.252 mol) of N-methylpiperidine were placed in a 250 ml flask provided with a dropping funnel, reflux condenser and magnetic stirrer, and 15.1 g (0.12 mol) of dimethyl sulfate were added while stirring, with the internal temperature being kept below 30° C. by cooling in ice. The reaction mixture was subsequently heated at 120° C. under the intrinsic pressure in the autoclave for 6 hours. The solution obtained in this way was, after cooling, used directly in step b) or step c).

b) Preparation of N,N-dimethylpiperidinium hydroxide by reaction with barium hydroxide 32.07 g (0.1017 mol) of barium hydroxide (octahydrate) and 258.3 g of water were placed in a 500 ml stirred flask provided with a dropping funnel and the mixture was heated to 40° C. 38.5 g (0.1017 mol) of the aqueous solution of the sulfate prepared in step a) were added dropwise from the dropping funnel over a period of 30 minutes. Immediately after commencement of the addition, a snow-white finely pulverulent precipitate of barium sulfate formed. After the addition was complete, the reaction mixture was stirred at 40° C. for another 7 hours, cooled and the precipitate was filtered off with suction through a blue band filter. This gave 274 g of a clear, colorless solution of N,N-dimethylpiperidinium hydroxide. Titration of the solution with 0.1 HCl indicated a hydroxide number of 8.45%, corresponding to a yield of 89% of theory. The sulfate concentration was <1 ppm.

c) Preparation of N,N-dimethylpiperidinium hydroxide by reaction with an OH-laden ion exchanger 70 g of a 10% strength by weight aqueous solution of N,N-dimethylpiperidinium hydroxide, obtainable by dilution of the aqueous solution prepared in step a) with deionized water, were admixed with 60 ml of a strongly basic ion exchanger (Ambersep® 900 OH) in the OH form (loading: 0.59 eq/l), and the mixture was shaken at room temperature for 24 hours. The ion exchanger was subsequently filtered off. This gave an about 10% strength by weight aqueous solution of N,N-dimethylpiperidinium hydroxide. Analysis of the solution for sulfate indicated a sulfate content of <1 ppm, based on the solution.

Example 2 a) Preparation of tetramethylammonium sulfate 100 ml of distilled water and 12.6 g (0.1 mol) of dimethyl sulfate were placed in a 250 ml flask provided with a dropping funnel and magnetic stirrer, and 50.0 g (0.42 mol) of trimethylamine (as a 50% strength solution in water) was added dropwise over a period of 30 minutes while stirring, with the internal temperature being kept at 20° C. by cooling in ice. The reaction mixture was subsequently transferred to a 300 ml stirring autoclave and this was heated at 120° C. for 6 hours. The internal pressure rose to 9.1 bar during this time. After cooling and venting, the crude product mixture was evaporated on a rotary evaporator and the residue obtained was dried at 50° C. in an oil pump vacuum and subsequently stirred with 300 ml of acetone at room temperature for 2 hours. The acetone was then removed by suction filtration, the resulting solid was washed once again with 100 ml of acetone and subsequently dried in an oil pump vacuum. This gave 26.56 g of tetramethylammonium sulfate having a water content of 10.5% by weight. This corresponds to a yield of 97% of theory.

b) Preparation of tetramethylammonium hydroxide by means of an ion exchanger

A 20% strength by weight solution of tetramethylammonium sulfate in water (corresponding to 79 000 mg of sulfate/kg) is passed continuously (680 ml/h) through a column (length: 1 m, volume: 646 ml) filled with the anion exchanger Ambersep® 900 OH. The maximum measured sulfate content of the eluate was <1 mg/kg, and the maximum measured chloride content was 7 mg/kg. The anion exchanger was able to be regenerated by means of high-purity NaOH and reused for the anion exchange.

c) Preparation of tetramethylammonium hydroxide by means of electrolysis 1380 g of a 20% strength by weight solution of tetramethylammonium sulfate obtainable by the method described in step a) was placed in the middle chamber of an electrolysis apparatus having three chambers. The middle chamber was separated from the anolyte on the anode side by means of an FT-FAP anion exchange membrane (from FuMA-Tech). On the cathode side, the middle chamber was separated from the catholyte (product) by a CMV cation exchange membrane (Asahi-Glass). A DSA was employed as anode; the cathode was stainless steel. 5000 g of a 0.02 molar aqueous sulfuric acid were introduced as anolyte. 1250 g of a 1% strength by weight solution of tetramethylammonium hydroxide (electronic grade) in high-purity water were placed in the cathode circuit. The electrolysis was carried out at 81.2 Ah for 6 hours. 1592 g of an 11.7% strength by weight solution of tetramethylammonium hydroxide were then taken from the catholyte. The current yield based on the catholyte was 61.2%. The sulfate content of the catholyte was 3 ppm, and the iron concentration was about 10 ppm. The concentration of tetramethylammonium sulfate in the starting material circuit was 0.1% by weight. The final concentration of sulfuric acid in the anolyte was 2.2% by weight.

Example 3 a) Preparation of tetramethylammonium phosphate 100 ml of distilled water and 14.0 g (0.1 mol) of trimethyl phosphate were placed in a 250 ml flask provided with a dropping funnel and magnetic stirrer, and 60.0 g (0.508 mol) of trimethylamine were added dropwise while stirring, with the internal temperature being kept at 20° C. by cooling in ice. The reaction mixture was subsequently transferred to a 300 ml stirring autoclave and this was heated at 180° C. for 6 hours while stirring. The internal pressure rose to 25 bar during this time. After cooling and venting, the crude product mixture was evaporated on a rotary evaporator and the residue obtained was dried at 50° C. in an oil pump vacuum, giving a partly crystalline substance. This was stirred with 500 ml of acetone at room temperature for 24 hours. The acetone was subsequently removed by suction filtration under a nitrogen atmosphere, the resulting solid was once again washed with 100 ml of acetone and subsequently dried in an oil pump vacuum. This gave 29.51 g (92.3% of theory) of product. The solid obtained in step a) was dissolved in a concentration of 20% by weight in deionized water. The solution was passed through a column containing a basic anion exchanger. The eluate comprised tetramethylammonium hydroxide. The phosphate content of the solution, determined by elemental analysis, was less than 1 ppm.

Example 4

Preparation of N,N-dimethylmorpholinium hydroxide 100 ml of distilled water and 14.0 g (0.1 mol) of trimethyl phosphate were placed in a 250 ml flask provided with a dropping funnel and magnetic stirrer, and 60.0 g (0.508 mol) of trimethylamine were added dropwise while stirring, with the internal temperature being kept at 20° C. by cooling in ice. The reaction mixture was subsequently transferred to a 300 ml stirring autoclave and this was heated at 180° C. for 6 hours while stirring. The internal pressure rose to 25 bar during this time. After cooling and venting, the crude product mixture was evaporated on a rotary evaporator and the residue obtained was dried at 50° C. in an oil pump vacuum, giving a partly crystalline substance. This was stirred with 500 ml of acetone at room temperature for 24 hours. The acetone was subsequently removed by suction filtration under a nitrogen atmosphere, the resulting solid was once again washed with 100 ml of acetone and subsequently dried in an oil pump vacuum. This gave 29.51 g of N,N-dimethylmorpholinium sulfate (92.3% of theory). The solid was dissolved in water and reacted with barium hydroxide in a manner analogous to example 1 b). This gave an aqueous solution of N,N-dimethylmorpholinium hydroxide having a sulfate content (calculated from the sulfur content determined by elemental analysis) of <270 ppm. The barium content of the solution was likewise <1 ppm.

Example 5 a) Preparation of $C_{14}$-alkyltrimethylammonium sulfate 48.2 g (0.2 mol) of $C_{14}$-alkyldimethylamine together with 100 ml of distilled water were placed in a 250 ml flask provided with a dropping funnel and magnetic stirrer, and 12.6 g (0.1 mol) of dimethyl sulfate were added, with the internal temperature being kept at 20° C. by cooling in ice. The reaction mixture was subsequently transferred to a 300 ml stirring autoclave and this was heated at 180° C. for 6 hours while stirring. The internal pressure rose to 7.6 bar during this time. After cooling and venting, the crude product mixture was evaporated on a rotary evaporator and the residue obtained was dried at 50° C. in an oil pump vacuum. This gave 52.3 g (86% of theory) of product.

$^1$H-NMR (ppm, $D_2O$): 3.3 (m, 2H), 3.1 (s, 9H), 1.7 (m, 2H), 1.3-1.5 (m, 22H), 0.8 (t 3H)

b) Preparation of $C_{14}$-alkyltrimethylammonium hydroxide

The solid can be converted into the $C_{14}$-alkyltrimethylammonium hydroxide by reaction with barium hydroxide in aqueous solution in a manner analogous to example 1b) or by means of an ion exchanger in a manner analogous to example 1c).

Example 6

Preparation of bis(trimethylethanolammonium) sulfate (bis-choline sulfate)

19.6 g (0.22 mol) of dimethylaminoethanol together with 100 ml of methanol were placed in a reaction vessel at room temperature, and 12.6 g (0.1 mol) of dimethyl sulfate were added while stirring, with the internal temperature being kept below 30° C. by cooling in ice. The reaction mixture was stirred at 30° C. for another 30 minutes and was subsequently transferred to a 300 ml stirring autoclave which was heated at 130° C. for 10 hours while stirring. The internal pressure rose to 16 bar during this time. After cooling and venting, the crude product mixture was evaporated on a rotary evaporator, giving a white solid. This was washed with acetone and subsequently dried in an oil pump vacuum. This gave 27.93 g of bis(trimethylethanolammonium) sulfate (93% of theory).

Example 7 a) Preparation of bis(trimethylethanolammonium) sulfate by reaction in water 280.35 g (3.15 mol) of dimethylaminoethanol together with 1500 ml of water were placed in a reaction flask provided with a dropping funnel, reflux condenser and magnetic stirrer at room temperature, and 189.1 g (1.5 mol) of dimethyl sulfate were added over a period of 30 minutes while stirring, with the internal temperature being kept below 30° C. by cooling in ice. The reaction mixture was subsequently heated in an autoclave at 130° C. under the intrinsic pressure for 10 hours. The reaction product mixture was freed of water by means of a thin film evaporator (T=140° C., 540 ml/h, overhead temperature: 99° C.). Excess dimethylaminoethanol was removed under reduced pressure (2 mbar, 80° C.). The bis(trimethylethanolammonium) sulfate obtained was used directly for the anion exchange in step b).

b) Preparation of bis(trimethylethanolammonium) hydroxide by reaction with barium hydroxide.

1190 g (1.485 mol) of bis(trimethylammonium) sulfate as an approximately 45% strength solution in water together with 3200 g of water were placed in a stirred flask provided with a dropping funnel and 473 g (1.5 mol) of barium hydroxide (octahydrate) were added all at once to the solution. A white suspension was formed and this was stirred at 50° C. for 5 hours. After addition of 45 g of activated carbon, the suspension was stirred for another 2 hours and the precipitate was filtered off with suction through a blue band filter. This gave 4361 g of a solution of bis(trimethylethanolammonium) hydroxide (87.7% yield). Analysis of the solution for sulfate gave a sulfate content of 36 ppm.

c) Preparation of trimethylethanolammonium salicylate

In a stirred flask, 2000 g (1.195 mol) of trimethylethanolammonium hydroxide solution (7.23% of OH$^-$) were admixed with 164.9 g (1.195 mol) of salicylic acid at room temperature. The resulting solution was heated to 50° C. and stirred at this temperature for 2 hours. After evaporation under reduced pressure (60° C., 2 mbar), the trimethylethanolammonium salicylate was obtained as a white solid (282.4 g=98% yield).

Elemental Analysis:

| Element | % found | % calculated |
|---------|---------|--------------|
| C | 59.3 | 59.75 |
| O | 27.1 | 26.55 |
| N | 6.0 | 5.8 |
| H | 7.9 | 7.9 |

Example 8

Preparation of bis(dimethyldiethanolammonium) sulfate 26.62 g (0.22 mol) of N-methyldiethanolamine together with 100 ml of methanol were placed in a reaction vessel at room temperature, and 12.6 g (0.1 mol) of dimethyl sulfate were added while stirring, with the internal temperature being kept below 30° C. by cooling in ice. The reaction mixture was stirred at room temperature for a further 30 minutes and subsequently transferred to an autoclave. After reaction in the autoclave at a temperature of 160° C. and an internal pressure of 7 bar for 10 hours, the autoclave was cooled and vented and the solvent was removed under reduced pressure (60° C., 2 mbar). This gave 34.2 g of bis(dimethyldiethanolammonium) sulfate (94% of theory).

The invention claimed is:

1. A process for preparing a quaternary ammonium compound, which comprises
   a) reacting an amine compound comprising at least one sp$^3$-hybridized nitrogen atom with a dialkyl sulfate or trialkyl phosphate to give a quaternary ammonium compound which has at least some polyvalent anions and not more than 100 ppm monoalkylsulfate anions, wherein said amine compound is reacted with a dialkyl sulfate with participation of both alkyl groups of said dialkyl sulfate to give a quaternary ammonium compound having sulfate anions or wherein said amine compound is reacted with a trialkyl phosphate with participation of at least two of the alkyl groups of the trialkyl phosphate to give a quaternary ammonium compound having phosphate anions and/or not more than 100 ppm monoalkylphosphate anions, and
   b) subjecting the quaternary ammonium compound obtained in step a) to an anion exchange.

2. The process according to claim 1, wherein the amine compound used in step a) is of the general formula NR$^1$R$^2$R$^3$, where R$^1$, R$^2$ and R$^3$ are selected independently of one another from the group consisting of hydrogen, alkyl, cycloalkyl, heterocycloalkyl, aryl and hetaryl, or at least two of the radicals R$^1$, R$^2$ and R$^3$, together with the N atom to which they are bound, are part of a polycyclic compound.

3. The process according to claim 1, wherein the amine compound used in step a) bears at least one further substituent selected from the group consisting of hydroxyl groups, mercapto groups, ester groups, thioester groups and combinations thereof.

4. The process according to claim 3, wherein the amine compound used in step a) is selected the group consisting of from amino alcohols, amino thiols and esters thereof with inorganic acids choline O-phosphate, choline O-sulfate or O-phosphatidylcholine.

5. The process according to claim 1, wherein the quaternary ammonium compound obtained comprises at least one anion X$^{n-}$ in which n is an integer corresponding to the valence of the anion and is selected from the group consisting of OH$^-$, HSO$_4^-$, NO$_2^-$, NO$_3^-$, CN$^-$, OCN$^-$, NCO$^-$, SCN$^-$, NCS$^-$, PO$_4^{3-}$, HPO$_4^{2-}$, (H$_2$PO$_4^{\ 2-}$), H$_2$PO$_{3-}$, HPO$_3^{2-}$, BO$_3^{3-}$, (BO$_2$)$_3^{3-}$, B$_5$O$_6^-$, B$_5$O$_8^-$, B$_5$H$_4$O$_{10}^-$, [BF$_4$]$^-$, [BCl$_4$]$^-$, [B(C$_6$H$_5$)$_4$]$^-$, [PF$_6$]$^-$, [SbF$_6$]$^-$, [AsF$_6$]$^-$, [AlCl$_4$]$^-$, [AlBr$_4$]$^-$, [ZnCl$_3$]$^-$, dichlorocuprates(I) and (II), CO$_3^{2\ -}$, HCO$_3^-$, F$^-$, (R'—COO)$^-$, R'$_3$SiO$^-$, (R'—SO$_3$)$^-$ and [(R'—SO$_2$)$_2$N ]$^-$, where R' is alkyl, cycloalkyl or aryl.

6. The process according to claim 1, wherein the reaction in step a) is carried out at a temperature of at least 40° C.

7. The process according to claim 1, wherein in step a), the amine compound is firstly brought into contact with the dialkyl sulfate or the trialkyl phosphate at a temperature of not more than 30° C. and the resulting mixture is subsequently heated to a temperature of at least 40° C.

8. The process according to claim 1, wherein the reaction in step a) is carried out in an organic solvent, in water or in a mixture thereof.

9. The process according to claim 8, wherein the solvent comprises at least 30% by volume of water.

10. The process according to claim 1, wherein the reaction in step a) is carried out in the presence of an inert gas.

11. The process according to claim 1, wherein the process steps a) and b) are carried out in the absence of halide ions.

12. The process according to claim 1, wherein the anion exchange in step b) is effected by transprotonation, reaction with a metal salt, ion exchange chromatography, electrolytically or by means of a combination thereof.

13. The process according to claim 12, wherein the reaction with the metal salt is carried out in a solvent from which a metal sulfate formed from the metal of the metal salt and the sulfate anion crystallizes.

14. The process as defined in claim 1 for preparing high-purity aqueous tetraalkylammonium hydroxide solutions, wherein, in each case in water and in the absence of compounds and of materials which comprise or liberate halide ions,
   a) a trialkylamine compound is reacted with a dialkyl sulfate or trialkyl phosphate to give a high-purity aqueous tetraalkylammonium salt solution and b) the tetraalkylammonium salt solution obtained in step a) is subjected to an electrolytic anion exchange or ion exchange chromatography to replace the anions by hydroxide ions.

15. The process according to claim 4, wherein the amino compound is choline O-phosphate, choline O-sulfate or O-phosphatidylcholine.

16. The process according to claim 6, wherein the reaction temperature is at least 80° C.

17. The process according to claim 16, wherein the reaction temperature is in the range from 100 to 220° C.

18. The process of claim 1, wherein said quaternary ammonium compound obtained in step a) has not more than 10 ppm monoalkylsulfate anions.

19. The process of claim 18, wherein said quaternary ammonium compound obtained in step a) has not more than 1 ppm monoalkylsulfate anions.

20. The process of claim 1, wherein said quaternary ammonium compound has exclusively polyvalent anions.

21. The process of claim 1, wherein said quaternary ammonium compound is free of monoalkylsulfate anions.

22. A process for preparing a quaternary ammonium compound, which comprises
   a) reacting an amine compound comprising at least one $sp^3$-hybridized nitrogen atom with a dialkyl sulfate with participation of both alkyl groups of said dialkyl sulfate to give a quaternary ammonium compound having exclusively polyvalent anions, and
   b) subjecting the quaternary ammonium compound obtained in step a) to an anion exchange.

* * * * *